US 11,409,950 B2

(12) United States Patent
Bao et al.

(10) Patent No.: US 11,409,950 B2
(45) Date of Patent: Aug. 9, 2022

(54) ANNOTATING DOCUMENTS FOR PROCESSING BY COGNITIVE SYSTEMS

(71) Applicant: International Business Machines Corporation, Armonk, NY (US)

(72) Inventors: Sheng Hua Bao, San Jose, CA (US); Xianying Liu, Fremont, CA (US); Nan Liu, San Jose, CA (US); Ramani Routray, San Jose, CA (US); Tongkai Shao, San Jose, CA (US); Feng Wang, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 695 days.

(21) Appl. No.: 16/406,312

(22) Filed: May 8, 2019

(65) Prior Publication Data
US 2020/0356603 A1 Nov. 12, 2020

(51) Int. Cl.
*G06F 40/169* (2020.01)
*G06F 16/9032* (2019.01)
(Continued)

(52) U.S. Cl.
CPC .......... *G06F 40/169* (2020.01); *G06F 16/907* (2019.01); *G06F 16/90332* (2019.01); *G16H 70/40* (2018.01); *G16H 70/60* (2018.01)

(58) Field of Classification Search
CPC ............................................. G06F 16/90332
See application file for complete search history.

(56) References Cited

U.S. PATENT DOCUMENTS 9,569,416 B1 * 2/2017 Martin ................ G06F 9/451
9,606,990 B2 3/2017 Allen et al.
(Continued)

OTHER PUBLICATIONS

"BioNLP 2014 Workshop on Biomedical Natural Language Processing", ACL 2014, The 52nd Annual Meeting of the Association for Computational Linguistics, Jun. 27-28, 2014, Proceedings of the Workshop, 155 pages.

(Continued)

*Primary Examiner* — Douglas Godbold
(74) *Attorney, Agent, or Firm* — Stephen J. Walder, Jr.; Aaron Pontikos

(57) ABSTRACT

Mechanisms are provided to implement an annotation mechanism allows users to annotate documents with annotations for processing by a cognitive medical system. The annotation mechanism receives, via a user interface, a user selection of an electronic document for annotation, and determines one or more domains associated with the selected electronic document from an analysis of metadata associated with the selected electronic document. The annotation mechanism retrieves a predefined set of annotations associated with each determined domain, and presents the predefined set of annotations as user selectable elements. The annotation mechanism receives, via the user interface, a selection of one or more annotations in the predefined set of annotations to be associated with the selected portion of the selected electronic document, and generates annotation metadata associating the selected portion using the selected one or more annotations. The annotation mechanism then generates an annotated electronic document using the annotated metadata.

20 Claims, 4 Drawing Sheets

(51) Int. Cl.
  *G16H 70/60*  (2018.01)
  *G16H 70/40*  (2018.01)
  *G06F 16/907*  (2019.01)

(56) References Cited

U.S. PATENT DOCUMENTS

| | | | |
|---|---|---|---|
| 2011/0125734 A1 | 5/2011 | Duboue et al. | |
| 2014/0281877 A1* | 9/2014 | Burge | G06F 40/169 715/230 |
| 2015/0339034 A1* | 11/2015 | Garcia | G06F 3/04842 715/738 |
| 2015/0347375 A1* | 12/2015 | Tremblay | G06F 16/367 704/9 |
| 2016/0070688 A1* | 3/2016 | Yao | G06F 40/169 715/232 |
| 2016/0335403 A1* | 11/2016 | Mabotuwana | G16H 15/00 |
| 2017/0011026 A1 | 1/2017 | Byron et al. | |
| 2018/0011830 A1* | 1/2018 | Iida | G06F 40/268 |
| 2018/0025075 A1* | 1/2018 | Beller | G06F 16/3329 707/769 |
| 2018/0157641 A1 | 6/2018 | Byron et al. | |
| 2018/0357210 A1* | 12/2018 | Mankovich | G16H 10/60 |
| 2019/0213254 A1* | 7/2019 | Ray | G06N 3/0445 |
| 2020/0312298 A1* | 10/2020 | Bui | G06F 40/169 |

OTHER PUBLICATIONS

Anonymously, "A Tool for assisted partitioning of documents into business defined subsets", IP.com No. IPCOM000227916D, IP.com Electronic Publication Date: May 29, 2013, 13 pages.

Anonymously, "Collaboration Annotation Enhancement", IP.com No. IPCOM000223756D, IP.com Electronic Publication Date: Nov. 28, 2012, 5 pages.

Anonymously, "Method of Annotating an Event with a Personal Activity Metadata in an Access Controlled Fashion", IP.com No. IPCOM000202109D, IP.com Electronic Publication Date: Dec. 3, 2010, 4 pages.

High, Rob, "The Era of Cognitive Systems: An Inside Look at IBM Watson and How it Works", IBM Corporation, Redbooks, Dec. 12, 2012, 16 pages.

Shang, Ning, "Integrating Domain Knowledge to Improve Signal Detection from Electronic Health Records for Pharmacovigilance", UT SBMI Dissertations (Open Access). 26. https://digitalcommons.library.tmc.edu/uthshis_dissertations/26, Summer 2014, 182 pages.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

* cited by examiner

ANNOTATING DOCUMENTS FOR PROCESSING BY COGNITIVE SYSTEMS

BACKGROUND

The present application relates generally to an improved data processing apparatus and method and more specifically to mechanisms for annotating documents for processing by cognitive systems.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples, of QA systems are Siri® from Apple®, Cortana® from Microsoft®, and question answering pipeline of the IBM Watson™ cognitive system available from International Business Machines (IBM®) Corporation of Armonk, N.Y. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypothesis based on the decomposed question and results of a primary search of answer sources, performs hypothesis and evidence scoring based on a retrieval of evidence from evidence sources, performs synthesis of the one or more hypothesis, and based on trained models, performs a final merging and ranking to output an answer to the input question along with a confidence measure.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions that are executed by the at least one processor to cause the at least one processor to be configured to implement an annotation mechanism allows users to annotate documents with annotations for processing by a cognitive medical system. The method comprises receiving, by the annotation mechanism via a user interface associated with the annotation mechanism, a user selection of an electronic document for annotation by a user. The method also comprises determining, by the annotation mechanism, one or more domains associated with the selected electronic document from an analysis of metadata associated with the selected electronic document. Moreover, the method comprises retrieving, by the annotation mechanism, from an annotation set repository, a predefined set of annotations associated with each determined domain of the selected electronic document. In addition, the method comprises presenting, by the annotation mechanism, the predefined set of annotations associated with a portion of the selected electronic document being annotated by the user as user selectable elements of the user interface. The method also comprises receiving, by the annotation mechanism via the user interface, a selection of one or more annotations in the predefined set of annotations to be associated with the selected portion of the selected electronic document. Further the method comprises generating, by the annotation mechanism, annotation metadata associating the selected portion of the selected electronic document with the selected one or more annotations. Additionally, the method comprises generating, by the annotation mechanism, an annotated electronic document using the annotated metadata.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
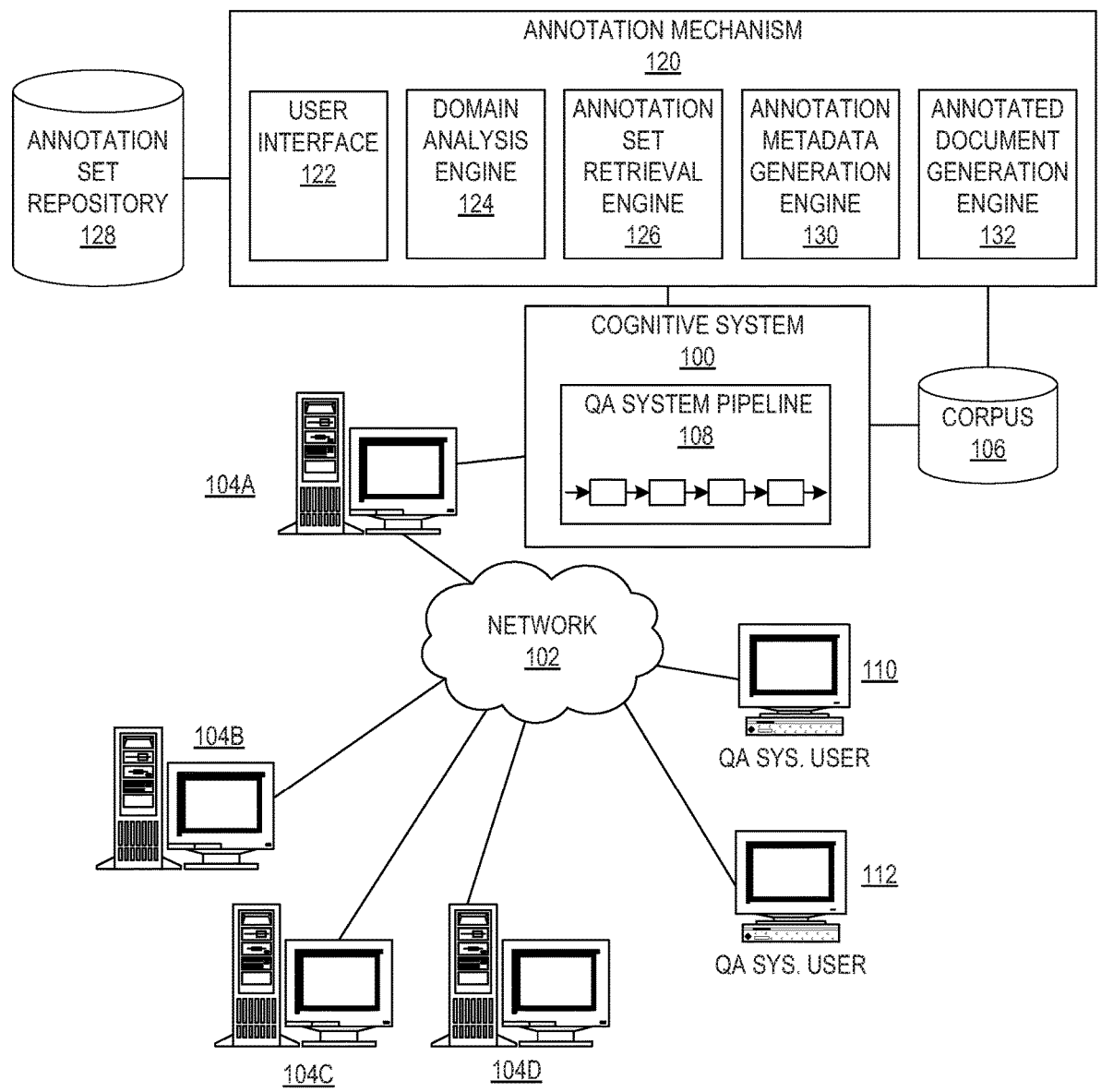
FIG. 1 depicts a schematic diagram of one illustrative embodiment of a cognitive system in a computer network.

In order to provide a corpus of documentation for use by a cognitive system when performing cognitive operations, it is important to be able to annotate the documentation such that the annotations may be utilized by the cognitive system when performing training and/or runtime processing of requests. However, current annotation methodologies involve human subject matter experts (SMEs) viewing the content of the documents and providing their own subjective annotations in a free form manner. This may lead to inconsistent usage of annotations across documents. Moreover, since the task of annotating a large corpus of documentation is a monumental task, often multiple SMEs are involved in performing the annotations, which may lead to conflicts and inconsistencies in annotations being made by multiple SMEs on the same or different documents.

In addition, in cases where multiple different SMEs may be annotating documents, these SMEs tend to want to use their own application environments to do the annotations. This may lead to problems in that some annotations may be lost during format conversions when other SMEs are attempting to annotate the same document, i.e. one SME may not see all of the annotations made by another SME to the document due to losses from format conversion.

The illustrative embodiments provide an annotation mechanism that allows users to annotate documents with annotations for processing by a cognitive medical system. The annotation mechanism minimizes conflicts between multiple human subject matter experts (SMEs) by providing a common set of annotations and a user interface through which such common annotations may be applied to portions of documents. In one implementation, this common set of annotations is a ribbon or bar type interface appearing at the top of a document view having annotations that are selectable for the particular domain of the document.

The illustrative embodiments support larger scale training document curation using auto-sourcing and allows the user to perform the annotation in the original format of the document rather than having to perform the annotations in a different format and perform a conversion. This is important because in some situations, through format conversion, some annotations may be lost. The illustrative embodiments also provide a user friendly tool for performing document annotation and reduce instances of conflicts in annotations performed by multiple different SMEs by providing a common set of annotations from which to select that are tied to the particular domain of the document.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides a labeling mechanism that allows users to annotate documents with annotations for processing by a cognitive medical system. The labeling mechanism minimizes conflicts between multiple human subject matter experts (SMEs) by providing a common set of annotations and a user interface through which such common annotations may be applied to portions of documents. In one implementation, this common set of annotations is a ribbon or bar type interface appearing at the top of a document view having annotations that are selectable for the particular domain of the document.

Figure 2:
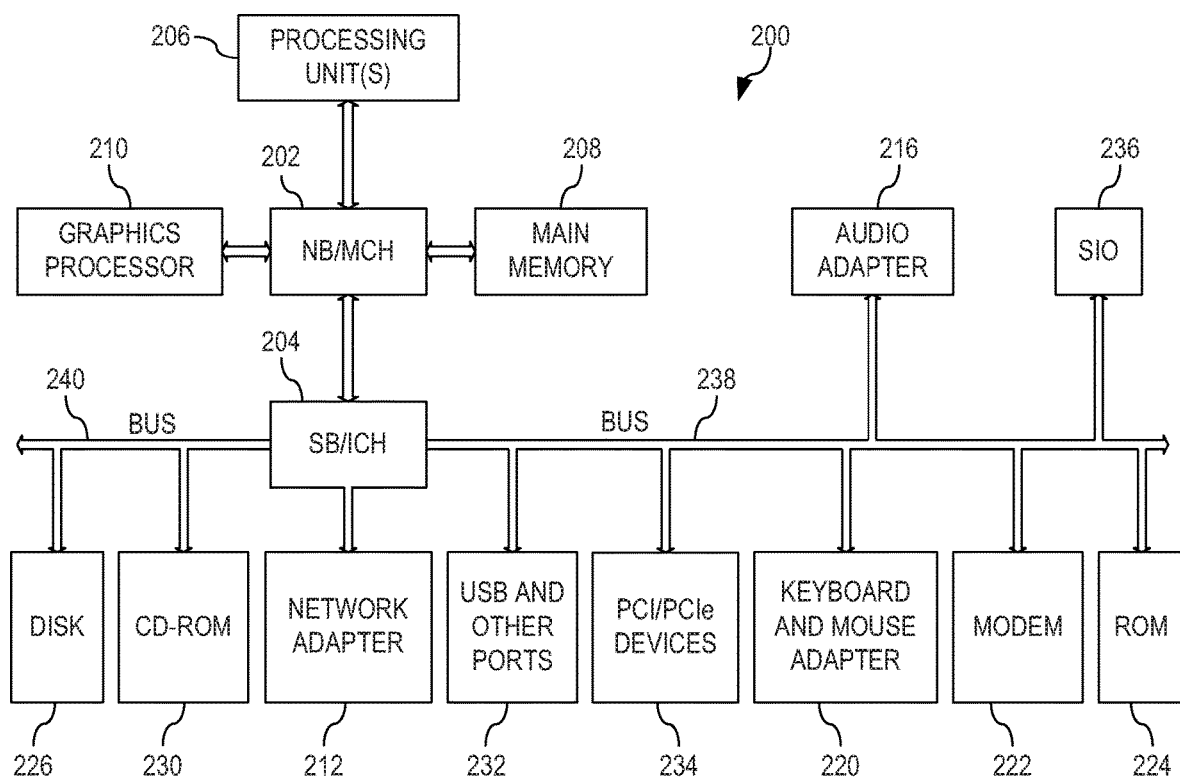
FIG. 2 is a block diagram of an example data processing system in which aspects of the illustrative embodiments are implemented.
Figure 3:
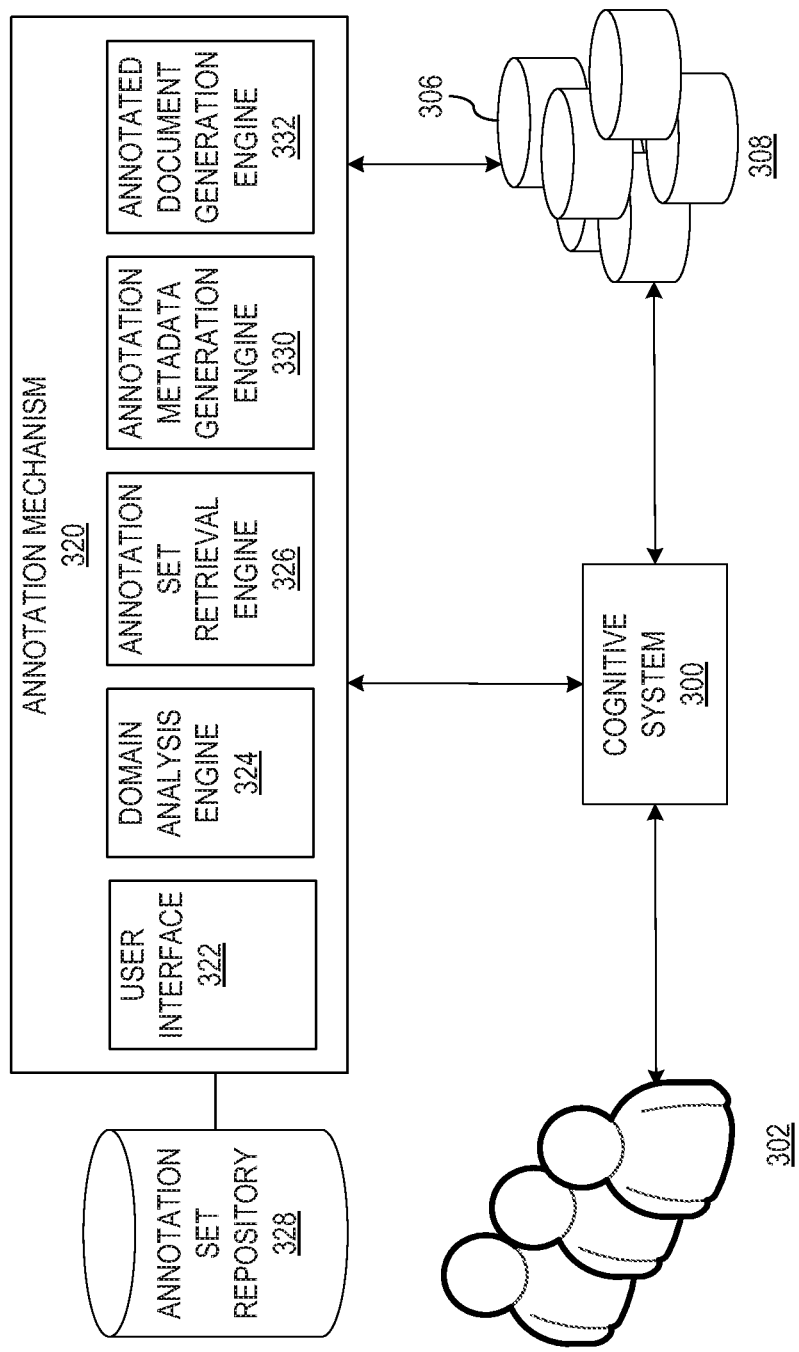
FIG. 3 is provided only as one example of the processing structure that may be implemented to allow users to annotate documents with annotations for processing by a cognitive medical system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example labeling mechanism for annotating documents for processing by cognitive systems. Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding
Ingest and process vast amounts of structured and unstructured data
Generate and evaluate hypothesis
Weigh and evaluate responses that are based only on relevant evidence
Provide situation-specific advice, insights, and guidance
Improve knowledge and learn with each iteration and interaction through machine learning processes
Enable decision making at the point of impact (contextual guidance)
Scale in proportion to the task
Extend and magnify human expertise and cognition
Identify resonating, human-like attributes and traits from natural language
Deduce various language specific or agnostic attributes from natural language
High degree of relevant recollection from data points (images, text, voice) (memorization and recall)
Predict and sense with situational awareness that mimic human cognition based on experiences
Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734. Which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D includes devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be bound in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing an annotation mechanism 120 that allows users to annotate documents with annotations for processing by a cognitive medical system. In operation, user interface 122 of annotation mechanism 120 receives a user selection of an electronic document for annotation by the user from corpus 106. Domain analysis engine 124 of annotation mechanism 120 then determines one or more domains associated with the selected electronic document from an analysis of metadata associated with the selected electronic document. If the selected electronic document comprises more than one domain, then each domain of the one or more domains may be associated with a specific portion of the selected electronic document and as such annotation set retrieval engine 126 of annotation mechanism 120 retrieves from annotation set repository 128 associated with annotation mechanism 120, a predefined set of annotations associated with each determined domain of the selected electronic document. User interface 122 then presents one of the retrieved predefined set of annotations as user selectable elements as the user annotates the specific portion of the selected electronic document associated with that retrieved predefined set of annotations. In one illustrative embodiment, user interface 122 provides a retrieved predefined set of annotations to the user via, for example, a ribbon, a menu bar, a pop-up, or the like, within the document view portion of user interface 122. User interface 122 may automatically switch the particular set of predefined annotations based on the particular domain of the selected electronic document and/or domain of the portion of the selected electronic document which is currently annotated. That is, user interface 122 may dynamically modify the predetermined set of annotations presented in user interface 122 in response to user selection of different portions of content in the selected electronic document based on the domains associated with the selected different portions of content in the selected electronic document.

As the user annotates the selected electronic document, user interface 122 receives a selection of portion, for example, a term, set of terms, or the like, of the electronic document and a selection of one or more annotations in the predefined set of annotations to be associated with that portion. Annotation metadata generation engine 130 of annotation mechanism 120 then generates annotation metadata associating the selected portion of the electronic document and the selected one or more annotations. In generating the annotation metadata, annotation metadata generation engine 130 may perform an annotation curation operation to reconcile the selected one or more annotations with one or more other annotations generated by one or more other users for the portion of the selected electronic document, other portions of the selected electronic document, or the selected electronic document as a whole. Performing the annotation curation operation may cause annotation metadata generation engine 130 to correlate different types of annotations selected by the user and generated by the one or more other users to identify a pattern of annotations, such that annotation metadata generation engine 130 generates annotation metadata specifying the pattern of annotations. In accordance with one illustrative embodiment, the pattern of annotations is a correlation of an annotation specifying a drug name, an annotation specifying an adverse event, and an annotation specifying a relationship between the drug name and the adverse event.

Annotated document generation engine 132 then generates an annotated electronic document that comprises the data from the selected electronic document and the annotation metadata. In generating the annotated electronic document, annotated document generation engine 132 automatically converts the annotations selected by the user to a format useable by a cognitive system 100, e.g., an XML document that maps the annotation to the term associated with that portion of the selected electronic document. Annotated document generation engine 132 may then store the annotated electronic document in corpus 106 such that, in one embodiment, cognitive system 100 processes the annotation metadata to perform a cognitive operation based on the annotation metadata. In another embodiment, the annotated electronic document may be used to train cognitive system 100.

In order to provide one example of the operation of the illustrative embodiment, an electronic document is selected for annotation by a team of SMEs. The document, e.g., patient health information document, is distributed to a trusted crowd of SMEs who each use the specialized annotation mechanism of the illustrative embodiment to annotate the content in the selected electronic document. The domain of the document may be specified in metadata of the document such that when the document is presented to the SMEs for annotation using the tool, the corresponding set of predefined common annotations are presented to each SME for their selection and association with content of the document. Each SME then annotates the portion of the document for which they are responsible and returns the annotated document back to the document curation system. The SME added annotations are then analyzed and reconciled by the annotation mechanism such that corresponding annotations are generated for use by the cognitive system. Thus, for example, one SME may annotate drug names in the document. Another SME may annotate adverse events in the document. A third SME may annotate a relationship between the drug and the adverse event. These annotations may then be reconciled by the annotation mechanism to represent an adverse drug reaction based on the correlation of the drug, the adverse event, and the relationship.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is provided only as one example of the processing structure that may be implemented to allow users to annotate documents with annotations for processing by a cognitive medical system in accordance with one illustrative embodiment. As shown in FIG. 3, the cognitive system 300 is further augmented, in accordance with the mechanisms of the illustrative embodiments, to include logic implemented in specialized hardware, software executed on hardware, or any combination of specialized hardware and software executed on hardware, for implementing an annotation mechanism 320 that allows users to annotate documents with annotations for processing by a cognitive medical system in accordance with one illustrative embodiment. In operation, user interface 322 of annotation mechanism 320 receives a user selection by user 302 of an electronic document for annotation by user 302 from a corpus 306.

Corpora 308 may be one or more databases storing information about, the electronic texts, documents, articles, websites, and the like, that make up the corpora of data/information 308. That is, these various sources themselves, different collections of sources, and the like, represent a different corpus 306 within the corpora 308. There may be different corpus 306 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 308 within the corpora 306.

Domain analysis engine 324 of annotation mechanism 320 then determines one or more domains associated with the selected electronic document from an analysis of metadata associated with the selected electronic document. If the selected electronic document comprises more than one domain, then each domain of the one or more domains may be associated with a specific portion of the selected electronic document and as such annotation set retrieval engine 326 of annotation mechanism 320 retrieves from annotation set repository 328 associated with annotation mechanism 320, a predefined set of annotations associated with each determined domain of the selected electronic document. User interface 322 then presents one of the retrieved predefined set of annotations as user selectable elements as user 302 annotates the specific portion of the selected electronic document associated with that retrieved predefined set of annotations. In one illustrative embodiment, user interface 322 provides a retrieved predefined set of annotations to user 302 via, for example, a ribbon, a menu bar, a pop-up, or the like, within the document view portion of user interface 322. User interface 322 may automatically switch the particular set of predefined annotations based on the particular domain of the selected electronic document and/or domain of the portion of the selected electronic document which is currently annotated. That is, user interface 322 may dynamically modify the predetermined set of annotations presented in user interface 322 in response to user selection of different portions of content in the selected electronic document based on the domains associated with the selected different portions of content in the selected electronic document.

As user 302 annotates the selected electronic document, user interface 322 receives a selection of portion, for example, a term, set of terms, or the like, of the electronic document and a selection of one or more annotations in the predefined set of annotations to be associated with that portion. Annotation metadata generation engine 330 of annotation mechanism 320 then generates annotation metadata associating the selected portion of the electronic document and the selected one or more annotations. In generating the annotation metadata, annotation metadata generation engine 330 may perform an annotation curation operation to reconcile the selected one or more annotations with one or more other annotations generated by one or more other users 302 for the portion of the selected electronic document, other portions of the selected electronic document, or the selected electronic document as a whole. Performing the annotation curation operation may cause annotation metadata generation engine 330 to correlate different types of annotations selected by user 302 and generated by the one or more other users 302 to identify a pattern of annotations, such that annotation metadata generation engine 330 generates annotation metadata specifying the pattern of annotations. In accordance with one illustrative embodiment, the pattern of annotations is a correlation of an annotation specifying a drug name, an annotation specifying an adverse event, and an annotation specifying a relationship between the drug name and the adverse event.

Annotated document generation engine 332 then generates an annotated electronic document that comprises the data from the selected electronic document and the annotation metadata. In generating the annotated electronic document, annotated document generation engine 332 automatically converts the annotations selected by user 302 to a format useable by a cognitive system 300, e.g., an XML document that maps the annotation to the term associated with that portion of the selected electronic document. Annotated document generation engine 332 may then store the annotated electronic document in corpus 306 such that, in one embodiment, cognitive system 300 processes the annotation metadata to perform a cognitive operation based on the annotation metadata. In another embodiment, the annotated electronic document may be used to train cognitive system 300.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement, the functions/acts specified in the flowchart and/or block diagram block or blocks.

Figure 4:
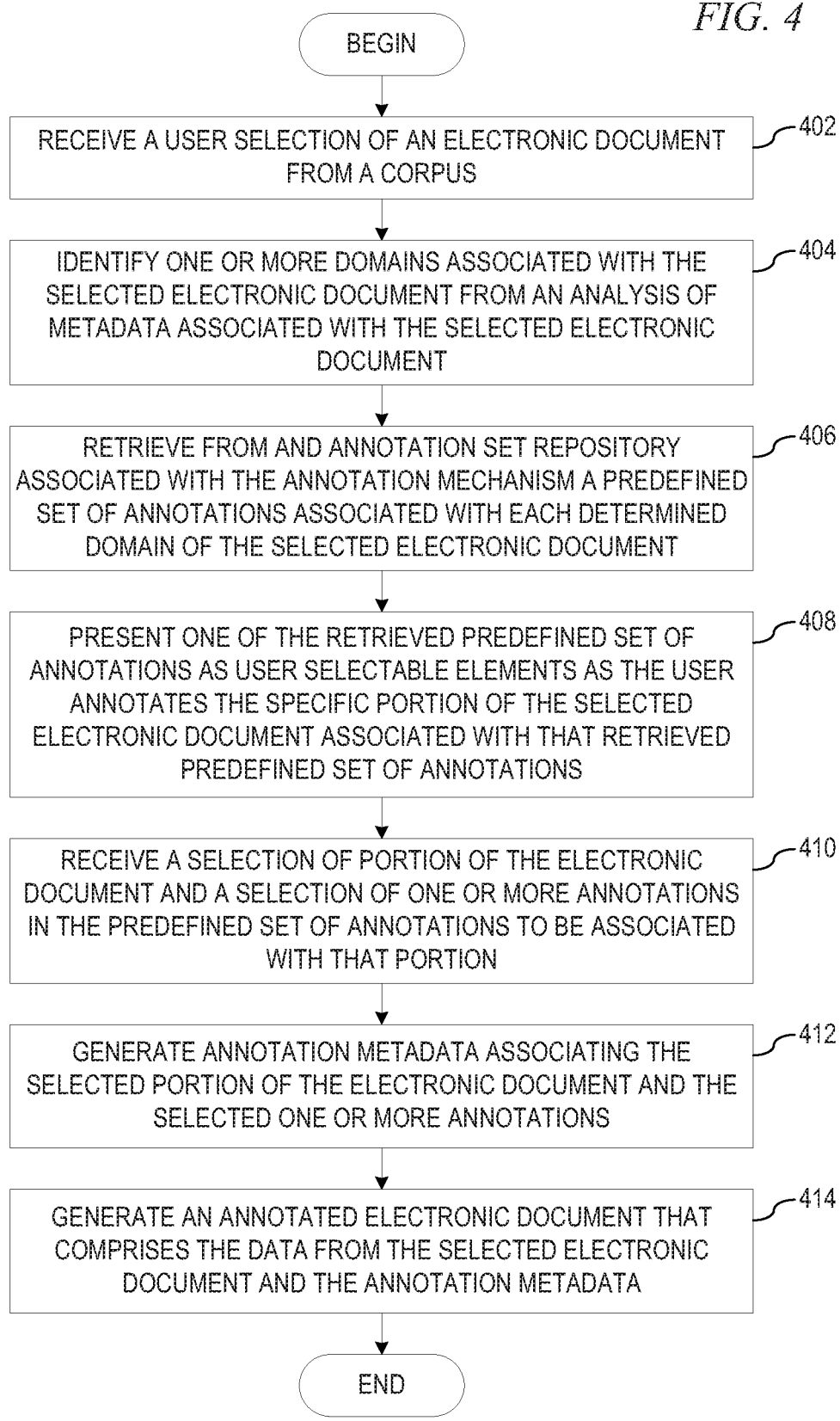
FIG. 4 depicts an exemplary flowchart of the operation performed by an annotation mechanism in allowing users to annotate documents with annotations for processing by a cognitive medical system in accordance with one illustrative embodiment.

FIG. 4 depicts an exemplary flowchart of the operation performed by an annotation mechanism in allowing users to annotate documents with annotations for processing by a cognitive medical system in accordance with one illustrative embodiment. As the operation begins, a user interface of the annotation mechanism receives a user selection of an electronic document from a corpus (step 402). A domain analysis engine of the annotation mechanism then identify one or more domains associated with the selected electronic document from an analysis of metadata associated with the selected electronic document (step 404). If the selected electronic document comprises more than one domain, then each domain of the one or more domains may be associated with a specific portion of the selected electronic document. Thus, an annotation set retrieval engine of the annotation mechanism retrieves from and annotation set repository associated with the annotation mechanism a predefined set of annotations associated with each determined domain of the selected electronic document (step 406).

The user interface then presents one of the retrieved predefined set of annotations as user selectable elements as the user annotates the specific portion of the selected electronic document associated with that retrieved predefined set of annotations (step 408). In one illustrative embodiment, the user interface provides a retrieved predefined set of annotations to the user via, for example, a ribbon, a menu bar, a pop-up, or the like, within the document view portion of the user interface. The user interface may automatically switch the particular set of predefined annotations based on the particular domain of the selected electronic document and/or domain of the portion of the selected electronic document which is currently annotated. That is, the user interface may dynamically modify the predetermined set of annotations presented in the user interface in response to user selection of different portions of content in the selected electronic document based on the domains associated with the selected different portions of content in the selected electronic document.

As the user annotates the selected electronic document, the user interface receives a selection of portion, for example, a term, set of terms, or the like, of the electronic document and a selection of one or more annotations in the predefined set of annotations to be associated with that portion (step 410). An annotation metadata generation engine of the annotation mechanism then generates annotation metadata associating the selected portion of the electronic document and the selected one or more annotations (step 412). In generating the annotation metadata, the annotation metadata generation engine may perform an annotation curation operation to reconcile the selected one or more annotations with one or more other annotations generated by one or more other users for the portion of the selected electronic document, other portions of the selected electronic document, or the selected electronic document as a whole. Performing the annotation curation operation may cause the annotation metadata generation engine to correlate different types of annotations selected by the user and generated by the one or more other users to identify a pattern of annotations, such that the annotation metadata generation engine generates annotation metadata specifying the pattern of annotations. In accordance with one illustrative embodiment, the pattern of annotations is a correlation of an annotation specifying a drug name, an annotation specifying an adverse event, and an annotation specifying a relationship between the drug name and the adverse event.

The annotated document generation engine then generates an annotated electronic document that comprises the data from the selected electronic document and the annotation metadata (step 414). In generating the annotated electronic document, the annotated document generation engine automatically converts the annotations selected by the user to a format useable by the cognitive system, e.g., an XML document that maps the annotation to the term associated with that portion of the selected electronic document. The annotated document generation engine may then store the annotated electronic document in the corpus such that, in one embodiment, the cognitive system processes the annotation metadata to perform a cognitive operation based on the annotation metadata. In another embodiment, the annotated electronic document may be used to train the cognitive system. The operation ends thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for allowing users to annotate documents with annotations for processing by a cognitive medical system. The annotation mechanism minimizes conflicts between multiple human subject matter experts (SMEs) by providing a common set of annotations and a user interface through which such common annotations may be applied to portions of documents. In one implementation, this common set of annotations is a ribbon or bar type interface appearing at the top of a document view having annotations that are selectable for the particular domain of the document.

The illustrative embodiments support larger scale training document curation using auto-sourcing and allows the user to perform the annotation in the original format of the document rather than having to perform the annotations in a different format and perform a conversion. This is important because in some situations, through format conversion, some annotations may be lost. The illustrative embodiments also provide a user friendly tool for performing document annotation and reduce instances of conflicts in annotations performed by multiple different SMEs by providing a common set of annotations from which to select that are tied to the particular domain of the document.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor to cause the at least one processor to be configured to implement an annotation mechanism allows users to annotate documents with annotations for processing by a cognitive medical system, the method comprising:
receiving, by the annotation mechanism via a user interface associated with the annotation mechanism and output via a computing device associated with a user, a user selection of an electronic document for annotation by the user;
determining, by the annotation mechanism, domains associated with different portions of the selected electronic document from an analysis of metadata associated with the selected electronic document;
retrieving, by the annotation mechanism, from an annotation set repository, a corresponding predefined set of annotations associated with each determined domain of each portion of the selected electronic document to form selected document annotation sets, wherein the annotation set repository stores a plurality of different sets of annotations for a plurality of different domains and the corresponding predefined sets of annotations are selected from the plurality of different sets of annotations based on the determined domains of the portions of the selected electronic document, to form the selected document annotation sets;
presenting, by the annotation mechanism, a predefined set of annotations, from the selected document annotation sets, associated with a portion of the selected electronic document being annotated by the user, as user selectable elements of the user interface output by the computing device;
dynamically modifying, by the annotation mechanism, the user interface, based on a user navigation input that navigates from one portion of the selected electronic document to another and selects a different currently selected portion of the electronic document for annotation, to automatically change the user selectable elements of the user interface to correspond to the particular set of annotations corresponding to a domain of the currently selected portion of the selected electronic document;
receiving, by the annotation mechanism via the user interface, a selection of one or more user selectable elements of the user interface currently being presented to thereby associate one or more annotations in the predefined set of annotations, corresponding to the selected one or more user selectable elements of the user interface, with the currently selected portion of the selected electronic document;
generating, by the annotation mechanism, annotation metadata associating the currently selected portion of the selected electronic document to the one or more annotations corresponding to the selected one or more user selectable elements of the user interface; and
generating, by the annotation mechanism, an annotated electronic document using the annotated metadata.

2. The method of claim 1, further comprising:
inputting, by the annotation mechanism, the annotated electronic document to a cognitive system which processes the annotation metadata to perform a cognitive operation based on the annotation metadata.

3. The method of claim 2, wherein the cognitive operation is generating a candidate answer to an input natural language question, wherein the candidate answer is generated based on the one or more annotations in the annotation metadata.

4. The method of claim 1, wherein generating the annotation metadata further comprises:
performing, by the annotation mechanism, an annotation curation operation to reconcile the one or more annotations corresponding to the selected one or more user selectable elements of the user interface with one or more other annotations generated by one or more other users for the portion of the selected electronic document, other portions of the selected electronic document, or the selected electronic document as a whole.

5. The method of claim 4, wherein performing the annotation curation operation comprises correlating, by the annotation mechanism, different types of annotations selected by the user and generated by the one or more other users to identify a pattern of annotations, and generating, by the annotation mechanism, annotation metadata specifying the pattern of annotations.

6. The method of claim 5, wherein the pattern of annotations is a correlation of an annotation specifying a drug name, an annotation specifying an adverse event, and an annotation specifying a relationship between the drug name and the adverse event.

7. The method of claim 1, wherein presenting the predefined set of annotations as user selectable elements of the user interface comprises presenting, by the annotation mechanism, the predefined set of annotations as a ribbon bar in the user interface.

8. The method of claim 1, presenting the predefined set of annotations further comprises:
  presenting, to a plurality of users via a plurality of user interfaces output on a plurality of different computing devices, the selected document annotation sets in response to the plurality of users selecting the selected electronic document, wherein at least two of the users in the plurality of users execute different software application environments to annotate the selected electronic document, and wherein the selected document annotation sets are presented to each of the users in the plurality of users via a common set of user selectable elements of the plurality of user interfaces;
  receiving user selections of the user selectable elements of the plurality of user interfaces from the plurality of users via the plurality of user interfaces output on the plurality of different computing devices; and
  reconciling the user selections of the user selectable elements of the plurality of user interfaces to generate a reconciled set of document annotations, wherein the annotated electronic document is generated based on the reconciled set of document annotations.

9. A computer program product comprising a computer readable storage medium having a computer readable program stored therein, wherein the computer readable program, when executed on a data processing system, causes the data processing system to implement an annotation mechanism allows users to annotate documents with annotations for processing by a cognitive medical system, and further causes the data processing system to:
  receive, by the annotation mechanism via a user interface associated with the annotation mechanism and output via a computing device associated with a user, a user selection of an electronic document for annotation by the user;
  determine, by the annotation mechanism, domains associated with different portions of the selected electronic document from an analysis of metadata associated with the selected electronic document;
  retrieve, by the annotation mechanism, from an annotation set repository, a corresponding predefined set of annotations associated with each determined domain of each portion of the selected electronic document to form selected document annotation sets, wherein the annotation set repository stores a plurality of different sets of annotations for a plurality of different domains and the corresponding predefined sets of annotations are selected from the plurality of different sets of annotations based on the determined domains of the portions of the selected electronic document, to form the selected document annotation sets;
  present, by the annotation mechanism, a predefined set of annotations, from the selected document annotation sets, associated with a portion of the selected electronic document being annotated by the user, as user selectable elements of the user interface output by the computing device;
  dynamically modify, by the annotation mechanism, the user interface, based on a user navigation input that navigates from one portion of the selected electronic document to another and selects a different currently selected portion of the electronic document for annotation, to automatically change the user selectable elements of the user interface to correspond to the particular set of annotations corresponding to a domain of the currently selected portion of the selected electronic document;
  receive, by the annotation mechanism via the user interface, a selection of one or more user selectable elements of the user interface currently being presented to thereby associate one or more annotations in the predefined set of annotations, corresponding to the selected one or more user selectable elements of the user interface, with the currently selected portion of the selected electronic document;
  generate, by the annotation mechanism, annotation metadata associating the currently selected portion of the selected electronic document to the one or more annotations corresponding to the selected one or more user selectable elements of the user interface; and
  generate, by the annotation mechanism, an annotated electronic document using the annotated metadata.

10. The computer program product of claim 9, wherein the computer readable program further causes the data processing system to:
  input, by the annotation mechanism, the annotated electronic document to a cognitive system which processes the annotation metadata to perform a cognitive operation based on the annotation metadata.

11. The computer program product of claim 10, wherein the cognitive operation is generating a candidate answer to an input natural language question, wherein the candidate answer is generated based on the one or more annotations in the annotation metadata.

12. The computer program product of claim 9, wherein the computer readable program to generate the annotation metadata further causes the data processing system to:
  perform, by the annotation mechanism, an annotation curation operation to reconcile the one or more annotations corresponding to the selected one or more user selectable elements of the user interface with one or more other annotations generated by one or more other users for the portion of the selected electronic document, other portions of the selected electronic document, or the selected electronic document as a whole.

13. The computer program product of claim 12, wherein the computer readable program to perform the annotation curation operation further causes the data processing system to correlate, by the annotation mechanism, different types of annotations selected by the user and generated by the one or more other users to identify a pattern of annotations, and generate, by the annotation mechanism, annotation metadata specifying the pattern of annotations.

14. The computer program product of claim 13, wherein the pattern of annotations is a correlation of an annotation specifying a drug name, an annotation specifying an adverse event, and an annotation specifying a relationship between the drug name and the adverse event.

15. The computer program product of claim 9, wherein the computer readable program to present the predefined set of annotations as user selectable elements of the user interface further causes the data processing system to present, by the annotation mechanism, the predefined set of annotations as a ribbon bar in the user interface.

16. The computer program product of claim 9, presenting the predefined set of annotations further comprises:

presenting, to a plurality of users via a plurality of user interfaces output on a plurality of different computing devices, the selected document annotation sets in response to the plurality of users selecting the selected electronic document, wherein at least two of the users in the plurality of users execute different software application environments to annotate the selected electronic document, and wherein the selected document annotation sets are presented to each of the users in the plurality of users via a common set of user selectable elements of the plurality of user interfaces;

receiving user selections of the user selectable elements of the plurality of user interfaces from the plurality of users via the plurality of user interfaces output on the plurality of different computing devices; and reconciling the user selections of the user selectable elements of the plurality of user interfaces to generate a reconciled set of document annotations, wherein the annotated electronic document is generated based on the reconciled set of document annotations.

17. An apparatus comprising:

at least one processor; and at least one memory coupled to the at least one processor, wherein the at least one memory comprises instructions which, when executed by the at least one processor, cause the at least one processor to implement an annotation mechanism allows users to annotate documents with annotations for processing by a cognitive medical system, and further cause the at least one processor to:

receive, by the annotation mechanism via a user interface associated with the annotation mechanism and output via a computing device associated with a user, a user selection of an electronic document for annotation by the user;

determine, by the annotation mechanism, domains associated with different portions of the selected electronic document from an analysis of metadata associated with the selected electronic document;

retrieve, by the annotation mechanism, from an annotation set repository, a corresponding predefined set of annotations associated with each determined domain of each portion of the selected electronic document to form selected document annotation sets, wherein the annotation set repository stores a plurality of different sets of annotations for a plurality of different domains and the corresponding predefined sets of annotations are selected from the plurality of different sets of annotations based on the determined domains of the portions of the selected electronic document, to form the selected document annotation sets;

present, by the annotation mechanism, a predefined set of annotations, from the selected document annotation sets, associated with a portion of the selected electronic document being annotated by the user, as user selectable elements of the user interface output by the computing device;

dynamically modify, by the annotation mechanism, the user interface, based on a user navigation input that navigates from one portion of the selected electronic document to another and selects a different currently selected portion of the electronic document for annotation, to automatically change the user selectable elements of the user interface to correspond to the particular set of annotations corresponding to a domain of the currently selected portion of the selected electronic document;

receive, by the annotation mechanism via the user interface, a selection of one or more user selectable elements of the user interface currently being presented to thereby associate one or more annotations in the predefined set of annotations, corresponding to the selected one or more user selectable elements of the user interface, with the currently selected portion of the selected electronic document;

generate, by the annotation mechanism, annotation metadata associating the currently selected portion of the selected electronic document to the one or more annotations corresponding to the selected one or more user selectable elements of the user interface; and generate, by the annotation mechanism, an annotated electronic document using the annotated metadata.

18. The apparatus of claim 17, wherein the instructions further cause the processor to:

input, by the annotation mechanism, the annotated electronic document to a cognitive system which processes the annotation metadata to perform a cognitive operation based on the annotation metadata.

19. The method of claim 1, wherein the plurality of different sets of annotations, for a plurality of different domains, stored in the annotation set repository are common across a plurality of different application environments used by different users to annotate electronic documents.

20. The apparatus of claim 17, presenting the predefined set of annotations further comprises:

presenting, to a plurality of users via a plurality of user interfaces output on a plurality of different computing devices, the selected document annotation sets in response to the plurality of users selecting the selected electronic document, wherein at least two of the users in the plurality of users execute different software application environments to annotate the selected electronic document, and wherein the selected document annotation sets are presented to each of the users in the plurality of users via a common set of user selectable elements of the plurality of user interfaces;

receiving user selections of the user selectable elements of the plurality of user interfaces from the plurality of users via the plurality of user interfaces output on the plurality of different computing devices; and reconciling the user selections of the user selectable elements of the plurality of user interfaces to generate a reconciled set of document annotations, wherein the annotated electronic document is generated based on the reconciled set of document annotations.

\* \* \* \* \*